(12) United States Patent
Blick et al.

(10) Patent No.: US 9,532,150 B2
(45) Date of Patent: Dec. 27, 2016

(54) EARDRUM SUPPORTED NANOMEMBRANE TRANSDUCER

(71) Applicant: Wisconsin Alumni Research Foundation, Madison, WI (US)

(72) Inventors: Robert H. Blick, Madison, WI (US); Burke S. Richmond, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 617 days.

(21) Appl. No.: 13/785,551

(22) Filed: Mar. 5, 2013

(65) Prior Publication Data

US 2014/0254856 A1 Sep. 11, 2014

(51) Int. Cl.
*H04R 25/00* (2006.01)

(52) U.S. Cl.
CPC ..... *H04R 25/606* (2013.01); *A61B 2562/0204* (2013.01); *A61B 2562/028* (2013.01); *A61B 2562/164* (2013.01); *A61B 2562/166* (2013.01); *H04R 25/554* (2013.01); *H04R 25/75* (2013.01); *H04R 2225/51* (2013.01)

(58) Field of Classification Search
CPC ....... H04R 25/02; H04R 25/604; H04R 25/55; H04R 25/556; H04R 25/30; H04R 25/305; H04R 25/60; H04R 25/70; H04R 25/75; A61B 5/617; A61B 5/045; A61B 5/121–5/1268
USPC .................................. 381/314, 324, 328, 329
See application file for complete search history.

(56) References Cited

U.S. PATENT DOCUMENTS

| 4,729,366 A | * | 3/1988 | Schaefer | ................... A61F 2/18 600/25 |
| 5,259,032 A | * | 11/1993 | Perkins | ................ H04R 25/606 381/312 |
| 6,285,063 B1 | * | 9/2001 | Splett | ....................... H03H 9/58 257/415 |
| 6,372,609 B1 | | 4/2002 | Aga et al. | |
| 7,052,854 B2 | | 5/2006 | Melker et al. | |
| 7,344,491 B1 | | 3/2008 | Seeney et al. | |
| 7,812,353 B2 | | 10/2010 | Yuan et al. | |
| 7,894,914 B2 | | 2/2011 | Stahmann et al. | |
| 8,005,526 B2 | | 8/2011 | Martin et al. | |
| 8,649,875 B2 | * | 2/2014 | Sarvazyan | ........... A61B 8/0841 607/60 |

(Continued)

OTHER PUBLICATIONS

Rajesh, Gitanjaly, Surbhi: Nano-Bio-Technology Excellence in Health CareNano-BioTechnology Excellence in Health Care: A Review. The Internet Journal of Nanotechnology. 2005 vol. 1 No. 2. DOI: 10.5580/1314.

(Continued)

*Primary Examiner* — Davetta W Goins
*Assistant Examiner* — Oyesola C Ojo
(74) *Attorney, Agent, or Firm* — Boyle Fredrickson, S.C.

(57) ABSTRACT

A flexible membrane of piezoelectric material sized to be supported by and to conform to the eardrum. Electrodes on the membrane allow the membrane to function as an audio transducer stimulating the eardrum with an audio signal or detecting audio signals at the eardrum. Applications may include detecting a variety of pathophysiological and biomechanical features of the tissues of the tympanic membrane and regional integrated anatomy, detecting audio, physical and biological signals, and/or delivery a variety of therapeutic modalities.

22 Claims, 2 Drawing Sheets

(56) References Cited

U.S. PATENT DOCUMENTS

| | | | |
|---|---|---|---|
| 2002/0035340 A1* | 3/2002 | Fraden | A61B 5/01 600/549 |
| 2002/0043889 A1* | 4/2002 | Inoue | H03H 3/08 310/313 B |
| 2006/0009818 A1* | 1/2006 | Von Arx | A61B 5/0028 607/60 |
| 2007/0154030 A1* | 7/2007 | Moses | H04R 25/606 381/72 |
| 2007/0282172 A1* | 12/2007 | Toumazou | A61B 5/0031 600/300 |
| 2008/0062052 A1* | 3/2008 | Suzuki | G01L 1/005 343/702 |
| 2008/0199400 A1 | 8/2008 | Dyer et al. | |
| 2011/0170180 A1 | 7/2011 | Turner et al. | |

OTHER PUBLICATIONS

Technical Data Motion 501 XCL P, © Feb. 2012 AN, Siemens AG, Order No. A91SAT-01694-99T1-7600, Printed in Germany.

Poe, Pyykko: Nanotechnology and the treatment of inner ear diseases, © 2011 John Wiley & Sons, Inc., vol. 3, Mar./Apr. 2011, pp. 212-221.

"Acoustic Waves—From Microdevices to Helioseismology," Chapter 28 ("Surface Acoustic Waves and Nano-Electromechanical Systems," D. J. Kreft and R. H. Blick), edited by Prof. M. G. Beghi, Nov. 2011.

* cited by examiner

EARDRUM SUPPORTED NANOMEMBRANE TRANSDUCER

STATEMENT REGARDING FEDERALLY SPONSORED RESEARCH OR DEVELOPMENT

This invention was made with government support under FA9550-08-1-0337 awarded by the USAF/AFOSR. The government has certain rights in the invention.

BACKGROUND OF THE INVENTION

The present invention relates to nanomembrane transducers and in particular to an audio transducer that may be applied directly to the eardrum.

Monitoring and characterizing human body conditions, such as perceptions of pain, pressure, fluid sensations and sound perceptions, is an important aspect in many neurotology diagnosis and treatment plans.

With respect to hearing, understanding average and peak sound levels that are sensed (e.g., noise dosimeter) may be helpful in many cases for monitoring risks to hearing or changes in hearing and/or treating the ear (e.g., amplification, noise cancellation). An ear drum supported transducer may objectively characterize symptoms to aid diagnosis and guide treatment. For example, tinnitus is the perception of sound in the absence of a corresponding external sound source and may result from a wide range of underlying causes.

Objective tinnitus occurs in cases in which an actual sound is produced within the body and is audible to the patient, though practically may not be audible to the clinician. Objective tinnitus may arise, for example, from muscle spasms that cause clicks or crackling around the middle ear, as in "myoclonic tinnitus." Other forms of objective tinnitus include, for example, "pulsatile tinnitus" in which patients experience a sound that varies with some aspect of the vascular system (arterial or venous) and which may raise concern for a variety of vascular pathologies.

Subjective tinnitus, on the other hand, may arise from neural mechanisms in which a perceived sound has no corresponding external or internal mechanical source.

Even among experienced clinicians, given the non-specific nature of a broad range of auditory and vestibular symptoms, the absence of clinical instrumentation to objectively monitor and characterize symptoms represents a fundamental barrier to accurate diagnosis and improved treatment. In other cases, understanding audio conditions may be helpful in monitoring and/or treating other disorders of the head, neck and/or other parts of the body (e.g., pulse oximeter, sleep monitor, bioassay, electrical stimulation for otalgia or headache).

Clinic based tests of neurotological conditions have considerable limitations, including sensitivity, specificity and reliability, and presently offer limited and temporally constrained information about physiological and non-physiological function of the auditory and vestibular system in real word conditions. As a result, discrepancies between objective findings and subjective complaints are common. The inability to correlate objective measures of physiological states, including changes in environmental and internal conditions, with subjective symptoms in real world conditions limits advances in the characterization and management of a broad range of neurotological conditions.

SUMMARY OF THE INVENTION

The present invention provides a small and lightweight audio transducer or "audio-lens" membrane at a micro or nano scale that may be placed directly on the eardrum to stimulate and sense an audio environment. The membrane may be sized to minimize interference with the normal physical properties of the conductive hearing system and to allow intimate connection with the structure that it is measuring. In particular, the membrane may be a flexible piezoelectric material that naturally generates electricity when vibrated and produces vibrations when stimulated with electricity and/or electromagnetic radiation. The membrane may operate wirelessly, or wired electrodes may be directly attached. The membrane may be sized to adhere to a portion or the whole tympanic membrane.

In one embodiment the invention provides an audio transducer having a piezoelectric membrane sized to be supported by and to conform to the eardrum. At least two electrodes are attached to the piezoelectric membrane to exchange audio frequency electrical energy with the piezoelectric membrane corresponding to audio vibrations of the eardrum.

It is thus a feature of at least one embodiment of the invention to provide an audio transducer that may intimately contact the eardrum for precise measurements of the audio environment of the eardrum.

The electrodes may be in an interdigitated pattern.

It is thus a feature of at least one embodiment of the invention to provide a simple electrode structure applied to one side of the membrane that may serve as an interface to the piezoelectric material.

The audio transducer may further include an antenna coupled to the membrane and the electrodes for exchanging electrical energy with the electrodes.

It is thus a feature of at least one embodiment of the invention to allow wireless communication with the membrane, which may avoid connecting wires or the like and possible unintended pressure from attachment of those wires.

The membrane may be a semiconductor and may be doped to provide for an active semiconductor device incorporated into the membrane.

It is thus a feature of at least one embodiment of the invention to provide a membrane that may both serve as a transducer and as a substrate for integrated circuits that may be placed on the membrane.

The audio transducer may further include at least one of a temperature sensor and pressure sensor supported by the membrane.

It is thus a feature of at least one embodiment of the invention to provide for supplemental measurements of the environment of the eardrum that may enhance diagnosis or treatment of ear related conditions.

The audio transducer may further include a releasable mechanical carrier attached to a periphery of the membrane for supporting the membrane during placement of the membrane on the eardrum and subsequent removal.

It is thus a feature of at least one embodiment of the invention to permit the membrane to be light and flexible without risk of folding over during installation.

The membrane may be coated with a biocompatible coating.

It is thus a feature of at least one embodiment of the invention to permit the membrane to be constructed of electrically desirable materials while still maintaining biocompatibility.

When the membrane includes an antenna, the invention may be practiced with the steps of exchanging electrical energy with the electrodes from a remote source. This energy may be radiofrequency energy which is down converted on the membrane to an audio signal to be applied to the electrodes.

It is thus an object of the invention to provide a simple method of electrically stimulating the membrane with an external radiofrequency source.

In one embodiment, radiofrequency energy may be "scavenged" and converted to DC power from the radiofrequency energy to retransmit radiofrequency energy from the membrane indicating a membrane state.

It is thus a feature of at least one embodiment of the invention to permit sophisticated radiofrequency communication between the membrane and external device not limited to passive electrical field detection.

The membrane further includes a projection extending from a broad surface of the membrane used to grasp the projection with a placement tool to locate the membrane on the eardrum and then release the same, and again grasp the projection with the placement tool to remove the membrane from the eardrum.

These and other objects, advantages and aspects of the invention will become apparent from the following description. The particular objects and advantages described herein may apply to only some embodiments falling within the claims and thus do not define the scope of the invention. In the description, reference is made to the accompanying drawings which form a part hereof, and in which there is shown a preferred embodiment of the invention. Such embodiment does not necessarily represent the full scope of the invention and reference is made, therefore, to the claims herein for interpreting the scope of the invention.

DETAILED DESCRIPTION OF THE PREFERRED EMBODIMENT

Figure 1:
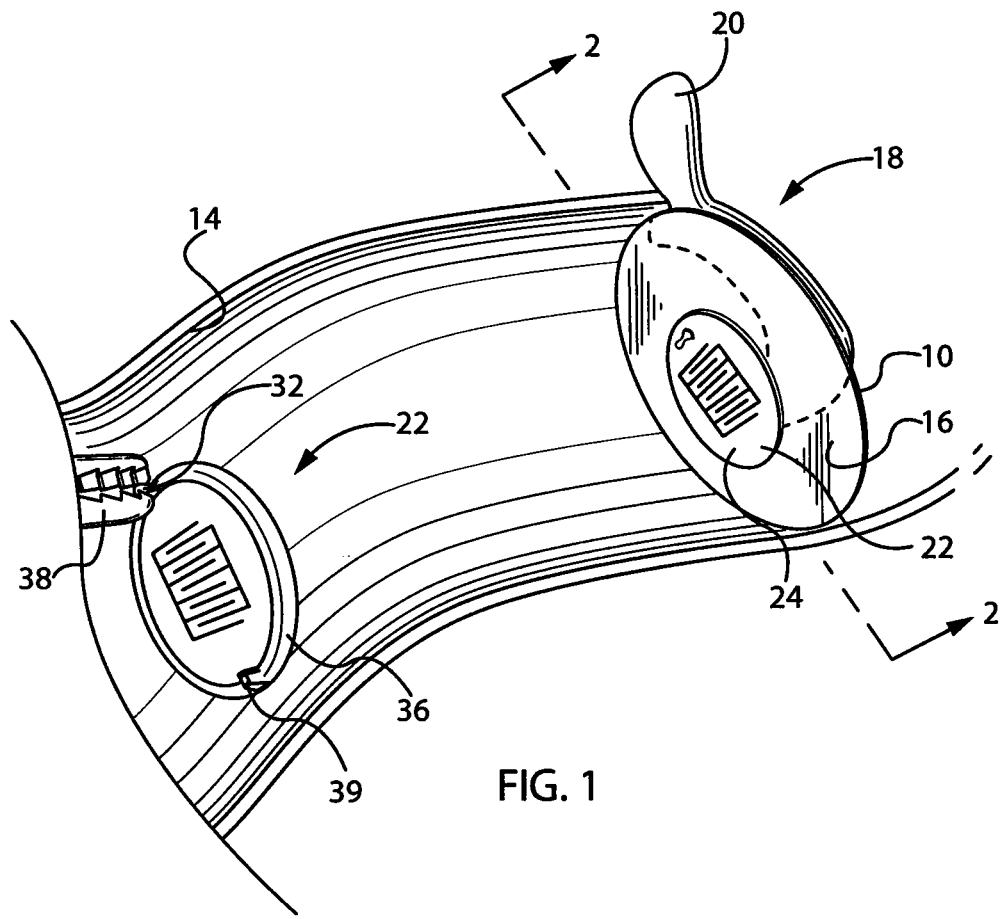
FIG. 1 is a perspective simplified view of the eardrum and ear canal showing an audio transducer of the present invention attached to the eardrum.

Referring now to FIG. 1, a human eardrum 10 (the "tympanic membrane") may span the end of an ear canal 14 for the receipt and detection of airborne audio signals through the ear canal 14 impinging on an outer surface 16 of the eardrum 10. A rear surface 18 of the eardrum 10 may contract a malleus bone 20 for communication of vibratory signals from the eardrum 10 to an inner ear structure that may sense those signals.

An audio transducer 22 of the present invention provides for a thin and flexible membrane 24 that may attach directly to an outer surface 16 of the eardrum 10, for example, through cohesive forces between a rear surface of the membrane 24 abutting the outer surface 16 of the eardrum 10, for example, promoted by moisture or oils on the outer surface 16 of the eardrum 10. As contacting the outer surface 16 of the eardrum 10, the membrane 24 maintains close conformance to the eardrum 10 resulting from its substantial flexibility to vibrate with the eardrum 10 without substantial modification to the acoustic properties of the eardrum 10. Alternative embodiments may provide other mechanisms for attachment, including micro- or nano-suction cups, or arrangements of hooks and loops.

In this regard, the membrane 24 may in one embodiment be a substantially circular disk having a diameter generally within the range of 0.5 millimeter to 10 millimeters, and in one embodiment substantially one millimeter, so that it may be placed on the outer surface 16 close to a center of the eardrum 10 (such as lateral to the umbo, being the most depressed part of the tympanic membrane, or draping over a substantial portion of the tympanic membrane) to experience substantial vibration while on a relatively smooth area of the eardrum outer surface 16 to which the flexible membrane 24 adheres. The membrane 24 may have a thickness of less than 1 µm and, in a preferred embodiment, a thickness of substantially 100 nm. It will be appreciated that other configurations than a circular disk may also be employed, for example a rectangular, square, trapezoidal, etc. shape, which may also advantageously reduce unwanted acoustical reflections with the membrane.

Figure 2:
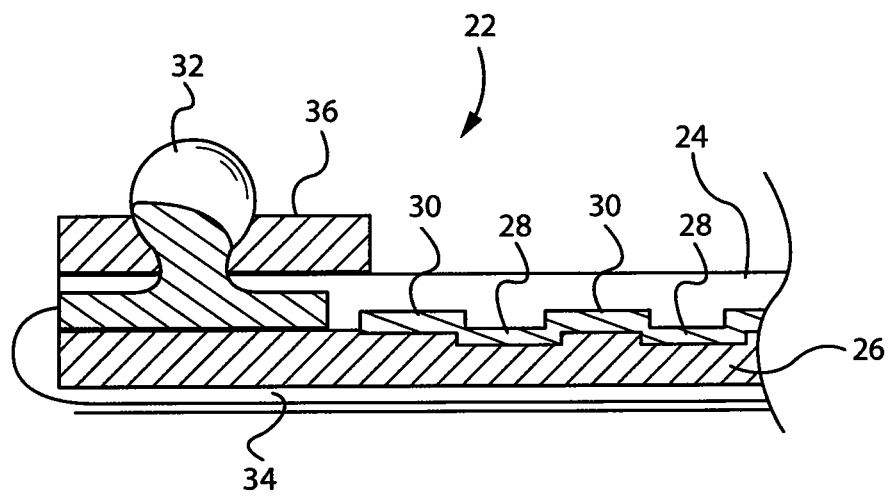
FIG. 2 is a cross-section along lines 2-2 of FIG. 1 showing a piezoelectric membrane of the audio transducer having doping, surface metallization, a biocompatible coating, a removal handle, and a support ring used in various embodiments of the invention.

Referring now also to FIG. 2, the membrane 24 may comprise an internal piezoelectric core 26 which, for example, may be a semiconductor, such as Silicon ("Si") or, in a preferred embodiment, may be a combination of a group III element with a group V element, such as the semiconductor compounds GaAs, InP, GaP and GaN, or a material such as PMN-PT as described in "Giant Piezoelectricity on Si for Hyperactive MEMS," S. H. Baek, J. Park, D. M. Kim, V. Aksyuk, R. R. Das, S. D. Bu, D. A. Felker, J. Lettieri, V. Vaithyanathan, S. S. N. Bharadwaja, N. Bassiri-Gharb, Y. B. Chen, H. P. Sun, C. M. Folkman, H. W. Jang, D. J. Kreft, S. K. Streiffer, R. Ramesh, X. Q. Pan, S. Trolier-McKinstry, D. G. Schlom, M. S. Rzchowski, R. H. Blick, C. B. Eom, Science 334, 958-961 (2011); DOI: 10.1126/science.1207186, hereby incorporated by reference. Methods of fabricating thin a piezoelectric core 26 of silicon are described, for example, in U.S. Pat. Application No. 2011/0170180 to Turner et al. citing U.S. Pat. No. 6,372,609 to Aga et al, all hereby incorporated by reference. Fabricating a piezoelectric core 26 of other semiconductors is enabled by U.S. Pat. No. 7,812,353 to Yuan et a., also hereby incorporated by reference.

Piezoelectricity refers to the charge that accumulates in certain solid materials, such as crystals, in response to applied mechanical stress. The piezoelectric effect is a reversible process in which substrates exhibiting the direct piezoelectric effect, such as internal generation of electrical charge resulting from an applied mechanical force, also exhibit the reverse piezoelectric effect, that is, internal generation of a mechanical strain that results from an applied electrical field.

The piezoelectric core 26 may be doped, for example, in regions 28 and may have metallization layers 30 together to fabricate electrical components such as resistors, transistors, diodes, small inductors, capacitors and memristors in the manner of an integrated circuit using standard integration circuit fabrication techniques. The metallization layers 30 may also provide for electrodes in contact with the piezoelectric core 26 for stimulating the core as will be described to produce mechanical flexure or detecting electrical fields caused by mechanical flexure of the piezoelectric core 26.

A handle 32 extending outward from a front surface of the audio transducer 22 may be attached to the piezoelectric core 26 for placement of the membrane 24 on the eardrum 10 has will be described. The piezoelectric core 26, doped regions 28, metallization electrodes 30 and portions of the handle 32 may all be conformably coated with a bio compatible coating 34 such as a Parylene coating preventing direct contact between non-biocompatible materials of the membrane 24 and tissue of the eardrum 10. Alternatively this coating may be applied solely on a rear face of the piezoelectric core 26 in contact with the outer surface 16 of the eardrum 10.

A carrier ring 36 may be optionally attached around a periphery of a front surface of the audio transducer 22 by a releasable adhesive to hold the otherwise flexible piezoelectric core 26 substantially flat without folding over onto itself during storage and installation.

Referring again to FIG. 1, the audio transducer 22 may be installed by grasping the handle 32 with forceps 38 (for example alligator forceps) while the carrier ring 36 is in place. Once the membrane 24 is attached to the surface of the eardrum 10, the carrier ring 36 may be removed by outwardly peeling away extending tabs 39 on a portion of the carrier ring 36.

Figure 3:
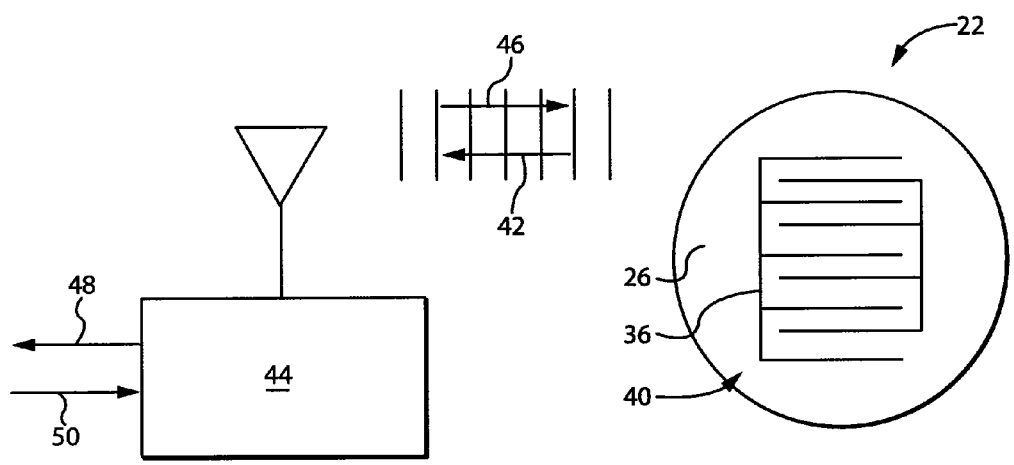
FIG. 3 is a simplified block diagram of a diagnostic system including a membrane of the present invention and an external radiofrequency transceiver for exchanging electrical energy and signals with the membrane.

Referring now to FIG. 3, in one embodiment, the metallization electrodes 30 may form a set of interdigitated but electrically separate electrodes 40 extending along a surface of the piezoelectric core 26. Such electrodes may form one or both of an antenna structure and sensing electrodes for sensing piezoelectric activity of the piezoelectric core 26 for stimulating electrodes for stimulating piezoelectric activity of the piezoelectric core 26. In this latter capacity, the interdigitated electrodes 40 may implement a surface acoustic wave device ("SAW"). A surface acoustic wave may be considered an acoustic wave traveling along the surface of a material exhibiting elasticity with an amplitude that typically decays exponentially with depth into the substrate. Surface acoustic waves produced in piezoelectric substrates in nano scale electromechanical systems are described in "Acoustic Waves—From Microdevices to Helioseismology," Chapter 28 ("Surface Acoustic Waves and Nano-Electromechanical Systems," D. J. Kreft and R. H. Blick), edited by Prof. M. G. Beghi, November 2011, which material is expressly incorporated by reference.

Mechanical stimulation of the piezoelectric core 26 from conducted audio vibrations energy from the eardrum 10, in this case, may produce electrical waveforms providing outgoing radio frequency energy 42 that may be detected by a sensitive radio transceiver 44, for example, positioned adjacent to the outer ear of the patient. Conversely, ingoing radio frequency energy 46 from the transceiver 44 may be received by the periodic structure of the interdigitated electrodes 40 to impress corresponding signals on the piezoelectric core 26 stimulating it into mechanical vibration. In this way the acoustic environment of the eardrum may be measured by audio output signals 48 received from the transceiver 44 derived from outgoing radiofrequency energy 42, and the audio environment of the eardrum may be affected by audio waveforms 50 provided to the transceiver 44 to produce the ingoing radio frequency energy 46.

Up conversion or down conversion between the outgoing radiofrequency energy 42 and 46 and the stimulation applied to the piezoelectric core 26 may be implemented by circuitry implemented on the piezoelectric core 26. This can allow the antenna 52 to operate in the megahertz or gigahertz range, reducing antenna size while producing audible stimulation to the electrodes 54 in the range of 20 hertz to 20 kilohertz. Conversely audio stimulation of the piezoelectric core 26 may be up converted allowing transmission of such audio signals through the antenna 52 in the megahertz or gigahertz range. Such up conversion and down conversion may make use of a nonlinear element to produce frequency harmonics or standard mixing or heterodyne technology. More advanced digital techniques such as pulse code modulation and frequency modulation may also be used.

Figure 4:
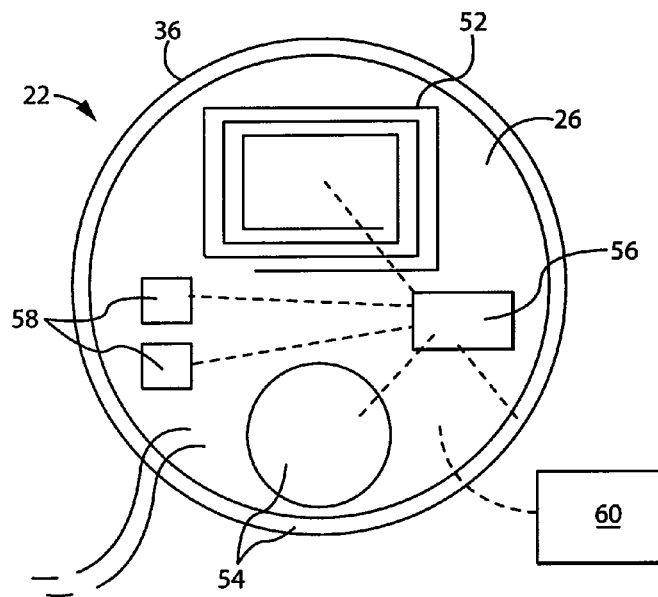
FIG. 4 is a block diagram of the components of some embodiments of the membrane implemented in a semiconductor in accordance with an embodiment of the present invention.

Referring now to FIG. 4, with respect to these more sophisticated signal processing techniques, it will be appreciated that the piezoelectric core 26 may support a variety of different elements including an arbitrarily designed antenna 52 produced using metallization electrodes 30 communicating with separately fabricated piezoelectric interface electrodes 54 which may be placed to produce desired modes of vibration or to detect desired modes of vibration of the piezoelectric core 26. Active circuitry 56 may, for example, scavenge power from the antenna 52 in the manner of an RFID (radiofrequency identification) tag to power heterodyne or mixing circuitry, and/or amplifiers to mediate between the antenna 52 and the electrodes 54. The active circuitry 56 may further include digital circuitry including analog to digital and digital to analog converting circuitry that may allow for digital communication over antenna 52 with the transceiver 44, small amounts of computer type memory and computer processing circuitry. In this regard additional sensor circuits 58 may be placed on the piezoelectric core 26 including, for example, pressure sensors, temperature sensors, accelerometers, optical electronics and the like. Some signal processing may be provided on the piezoelectric core 26 and multiplexing capabilities to transmit or receive different signals from the ear.

The antenna 52 may be augmented or replaced with a photoelectric detector which may also be used to provide a source of power. Micro-Electromechanical Systems (MEMS) technology supported on the piezoelectric core may be used to produce micro sampling circuitry or drug delivery circuitry, all activated by signals received over the antenna 52.

While the invention contemplates linkage using optical or radiofrequency signals, it will be appreciated that in a simplest embodiment, alternatively thin wires or conductive threads may be attached strictly to the electrodes 54 for similar purpose.

Together with or instead of fabricating circuitry directly on the piezoelectric core 26, the piezoelectric core 26 may communicate with a local circuit system 60, for example, supported by or otherwise in close proximity with the audio transducer 22 to effect additional processing and communication tasks. For example, the piezoelectric core 26 may communicate with the conventional RFID circuit resting within the ear canal 14.

Generally, the present invention may operate to detect vibrations of the eardrum, which may help to diagnose tinnitus subtypes or other conditions in patients, which may help to monitor the ear and diagnose patients. Alternatively, the invention may operate to provide direct excitations of the eardrum, which may help to relieve patients of pain. In some applications the invention may replace external ear probes, such as for otoacoustic emission testing, auditory brainstem response testing, electro-cochleaography, vestibular evoked myogenic responses, and others applications. As set forth above, various embodiments of the invention may include amplifying external sounds to the ear, as in an improved hearing aid, canceling undesirable sounds to the ear, as in a treatment for tinnitus or somatosensory disturbances, pain management, or improved "earplugs," and/or discreetly communicating with a person from a remote location, such as for military and/or security applications. Further embodiments may provide actuating elements for intelligent delivery of small medication doses to the eardrum, micro-sampling of blood, micro-sampling for drug testing and/or vital sign monitoring.

One or more specific embodiments of the present invention have been described above. It is specifically intended that the present invention not be limited to the embodiments and/or illustrations contained herein, but include modified forms of those embodiments including portions of the embodiments and combinations of elements of different embodiments as come within the scope of the following claims. It should be appreciated that in the development of any such actual implementation, as in any engineering or design project, numerous implementation-specific decisions must be made to achieve the developers' specific goals, such as compliance with system-related and business related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure. Nothing in this application is considered critical or essential to the present invention unless explicitly indicated as being "critical" or "essential."

Certain terminology is used herein for purposes of reference only, and thus is not intended to be limiting. For example, terms such as "upper," "lower," "above," and "below" refer to directions in the drawings to which reference is made. Terms such as "front," "back," "rear," "bottom," "side," "left" and "right" describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first," "second" and other such numerical terms referring to structures do not imply a sequence or order unless clearly indicated by the context.

When introducing elements or features of the present disclosure and the exemplary embodiments, the articles "a," "an," "the" and "said" are intended to mean that there are one or more of such elements or features. The terms "comprising," "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

References to "a microcontroller" or "the microcontroller" can be understood to include one or more microcontrollers that can communicate in a stand-alone and/or a distributed environment(s), and can thus be configured to communicate via wired or wireless communications with other processors, where such one or more processor can be configured to operate on one or more processor-controlled devices that can be similar or different devices. Furthermore, references to memory, unless otherwise specified, can include one or more microcontroller-readable and accessible memory elements and/or components that can be internal to the microcontroller-controlled device, external to the microcontroller-controlled device, and can be accessed via a wired or wireless network.

It is specifically intended that the present invention not be limited to the embodiments and illustrations contained herein and the claims should be understood to include modified forms of those embodiments including portions of the embodiments and combinations of elements of different embodiments as coming within the scope of the following claims. All of the publications described herein including patents and non-patent publications are hereby incorporated herein by reference in their entireties.

We claim:

1. An audio transducer comprising:
   a piezoelectric membrane sized to be supported by and to conform to an outer surface of a human eardrum;
   an antenna structure supported on the piezoelectric membrane;
   at least two sensing electrodes attached to the piezoelectric membrane and communicating with the antenna structure to exchange audio frequency electrical energy with the piezoelectric membrane corresponding to audio vibrations of the eardrum; and
   circuitry supported on the piezoelectric membrane for communicating with a device to exchange wireless radiofrequency electrical energy with the device, wherein the circuitry down converts the radiofrequency electrical energy to a signal in the audio range to be applied to the electrodes,
   wherein the piezoelectric membrane has a thickness less than the eardrum.

2. The audio transducer of claim 1, wherein the electrodes are in an interdigitated pattern.

3. The audio transducer of claim 1, further comprising an antenna coupled to the membrane and the electrodes for exchanging electrical energy with the electrodes.

4. The audio transducer of claim 1, wherein the membrane is a semiconductor.

5. The audio transducer of claim 4, wherein the membrane is doped to provide for an active semiconductor device incorporated into the membrane.

6. The audio transducer of claim 4, wherein the semiconductor is a combination of a group III element with a group V element.

7. An audio transducer comprising:
   a piezoelectric membrane sized to be supported by and to conform to an outer surface of a human eardrum;
   at least two electrodes provided in a conductive layer formed in a pattern supported on the piezoelectric membrane configured to exchange audio frequency electrical energy with the piezoelectric membrane corresponding to audio vibrations of the eardrum,
   wherein the membrane is a semiconductor having a thickness less than the eardrum; and
   further comprising at least one of a temperature sensor and a pressure sensor supported by the membrane.

8. An audio transducer comprising:
   a piezoelectric membrane sized to be supported by and to conform to an outer surface of a human eardrum;
   at least two electrodes provided in a conductive layer of the piezoelectric membrane configured to exchange audio frequency electrical energy with the piezoelectric membrane corresponding to audio vibrations of the eardrum; and a releasable mechanical carrier attached to a periphery of the membrane for supporting the membrane during placement of the membrane on the eardrum and subsequent removal,
wherein the membrane has a thickness less than the eardrum.

9. The audio transducer of claim 1, further including a biocompatible coating over the membrane.

10. The audio transducer of claim 1, wherein the membrane has a thickness of less than 1 μm.

11. A method for treatment of a human ear comprising:
(a) placing on an outer surface of a human eardrum in an ear canal a piezoelectric membrane sized to be supported by and to conform to the eardrum and having at least two electrodes provided in a conductive layer of the piezoelectric membrane configured to exchange electrical energy with the piezoelectric membrane corresponding to audio vibrations of the eardrum; and
(b) communicating with the electrodes at a device outside of the ear canal to exchange electrical energy with the electrodes formed by at least one of: audio stimulation of the eardrum and detection of sound at the eardrum,
wherein the energy is radiofrequency energy, and including the step of down converting the radiofrequency energy to a signal in the audio range to be applied to the electrodes, and
wherein the piezoelectric membrane has a thickness less than the eardrum.

12. The method of claim 11, wherein the electrodes are in an interdigitated pattern to detect or generate acoustic vibrations directed along a surface of the membrane.

13. The method of claim 11, wherein the membrane includes an antenna coupled to the membrane and the electrodes and further including the step of exchanging electrical energy with the electrodes from a remote source.

14. A method for treatment of a human ear comprising:
(a) placing on an outer surface of a human eardrum in an ear canal a piezoelectric membrane sized to be supported by and to conform to the eardrum and having at least two electrodes provided in a conductive layer of the piezoelectric membrane configured to exchange electrical energy with the piezoelectric membrane corresponding to audio vibrations of the eardrum; and
(b) communicating with the electrodes at a device outside of the ear canal to exchange electrical energy with the electrodes formed by at least one of: audio stimulation of the eardrum and detection of sound at the eardrum,
wherein the energy is radiofrequency energy, and including the step of scavenging DC power from the radiofrequency energy to retransmit radiofrequency energy from the membrane indicating a membrane state, and
wherein the piezoelectric membrane has a thickness less than the eardrum.

15. The method of claim 14, wherein the membrane state includes at least one of audio vibrations of the membrane, temperature of the membrane and pressure at the membrane.

16. A method for treatment of a human ear comprising:
(a) placing on an outer surface of a human eardrum in an ear canal a piezoelectric membrane sized to be supported by and to conform to the eardrum and having at least two electrodes provided in a conductive layer of the piezoelectric membrane configured to exchange electrical energy with the piezoelectric membrane corresponding to audio vibrations of the eardrum; and
(b) communicating with the electrodes at a device outside of the ear canal to exchange electrical energy with the electrodes formed by at least one of: audio stimulation of the eardrum and detection of sound at the eardrum,
wherein the membrane includes a releasable mechanical carrier attached to a periphery of the membrane for supporting the membrane during placement of the membrane on the eardrum, and including the step of removing the releasable mechanical carrier after attachment of the membrane to the eardrum, and
wherein the piezoelectric membrane has a thickness less than the eardrum.

17. A method for treatment of a human ear comprising:
(a) placing on an outer surface of a human eardrum in an ear canal a piezoelectric membrane sized to be supported by and to conform to the eardrum and having at least two electrodes provided in a conductive layer of the piezoelectric membrane configured to exchange electrical energy with the piezoelectric membrane corresponding to audio vibrations of the eardrum; and
(b) communicating with the electrodes at a device outside of the ear canal to exchange electrical energy with the electrodes formed by at least one of: audio stimulation of the eardrum and detection of sound at the eardrum,
wherein the membrane further includes a projection extending from a broad surface of the membrane, wherein step (a) includes grasping the projection with a placement tool to locate the membrane on the eardrum and then releasing the projection, and including step (c) after step (b) of again grasping the projection with the placement tool to remove the membrane from the eardrum, and
wherein the piezoelectric membrane has a thickness less than the eardrum.

18. The method of claim 14, wherein the electrodes are in an interdigitated pattern to detect or generate acoustic vibrations directed along a surface of the membrane.

19. The method of claim 14, wherein the membrane includes an antenna coupled to the membrane and the electrodes and further including the step of exchanging electrical energy with the electrodes from a remote source.

20. An audio transducer comprising:
a piezoelectric membrane sized to be supported by and to conform to an outer surface of a human eardrum;
at least two electrodes provided in a conductive layer of the piezoelectric membrane configured to exchange audio frequency electrical energy with the piezoelectric membrane corresponding to audio vibrations of the eardrum; and
circuitry supported on the piezoelectric membrane for scavenging DC power from radiofrequency energy to retransmit radiofrequency energy from the membrane indicating a membrane state,
wherein the piezoelectric membrane has a thickness less than the eardrum.

21. The audio transducer of claim 1, wherein the antenna structure and the at least two sensing electrodes are formed from common electrodes.

22. The audio transducer of claim 1, wherein the piezoelectric membrane is a substantially circular disk having a diameter allowing the membrane to span at least half of the eardrum.

* * * * *